United States Patent [19]
Dietrich et al.

[11] Patent Number: 4,722,096
[45] Date of Patent: Jan. 26, 1988

[54] APPARATUS FOR TRANSRADIATING OBJECTS ON A CONVEYOR PATH

[75] Inventors: Rolf Dietrich, Hofheim; Gerhard Doenges, Heidenrod-Kemel; Thomas Herwig, Eltville, all of Fed. Rep. of Germany

[73] Assignee: Heimann GmbH, Fed. Rep. of Germany

[21] Appl. No.: 824,465

[22] Filed: Jan. 31, 1986

[30] Foreign Application Priority Data

Mar. 4, 1985 [DE] Fed. Rep. of Germany ....... 3507611

[51] Int. Cl.$^4$ .................... G01N 23/10; G01N 23/04
[52] U.S. Cl. ....................................... 378/57; 378/58; 378/92; 378/99
[58] Field of Search ................ 378/57, 58, 92, 99; 250/358.1, 359.1, 360.1

[56] References Cited

U.S. PATENT DOCUMENTS

| | | | |
|---|---|---|---|
| 3,987,301 | 10/1976 | O'Connor | 250/227 |
| 4,430,568 | 2/1984 | Yoshida et al. | 378/57 |
| 4,599,740 | 7/1986 | Cable | 378/57 |

FOREIGN PATENT DOCUMENTS

| | | |
|---|---|---|
| 0077939 | 5/1983 | European Pat. Off. |
| 2490824 | 9/1981 | France |

Primary Examiner—Carolyn E. Fields
Assistant Examiner—Joseph A. Hynds
Attorney, Agent, or Firm—Hill, Van Santen, Steadman & Simpson

[57] ABSTRACT

An apparatus for transradiating an object moving on a conveyor path has a radiation generator for generating at least one fan-shaped radiation beam directed at the object and disposed substantially perpendicularly to the conveyor path, a number of line-shaped radiation detectors disposed for receiving radiation after passing through respective portions of the object with radiation passing through one portion of the object being received by one of the detectors, and all of the detectors in combination receiving all of the radiation passing through the object, and an evaluation unit connected to the detectors for evaluating signals therefrom to form an image of the object.

11 Claims, 2 Drawing Figures

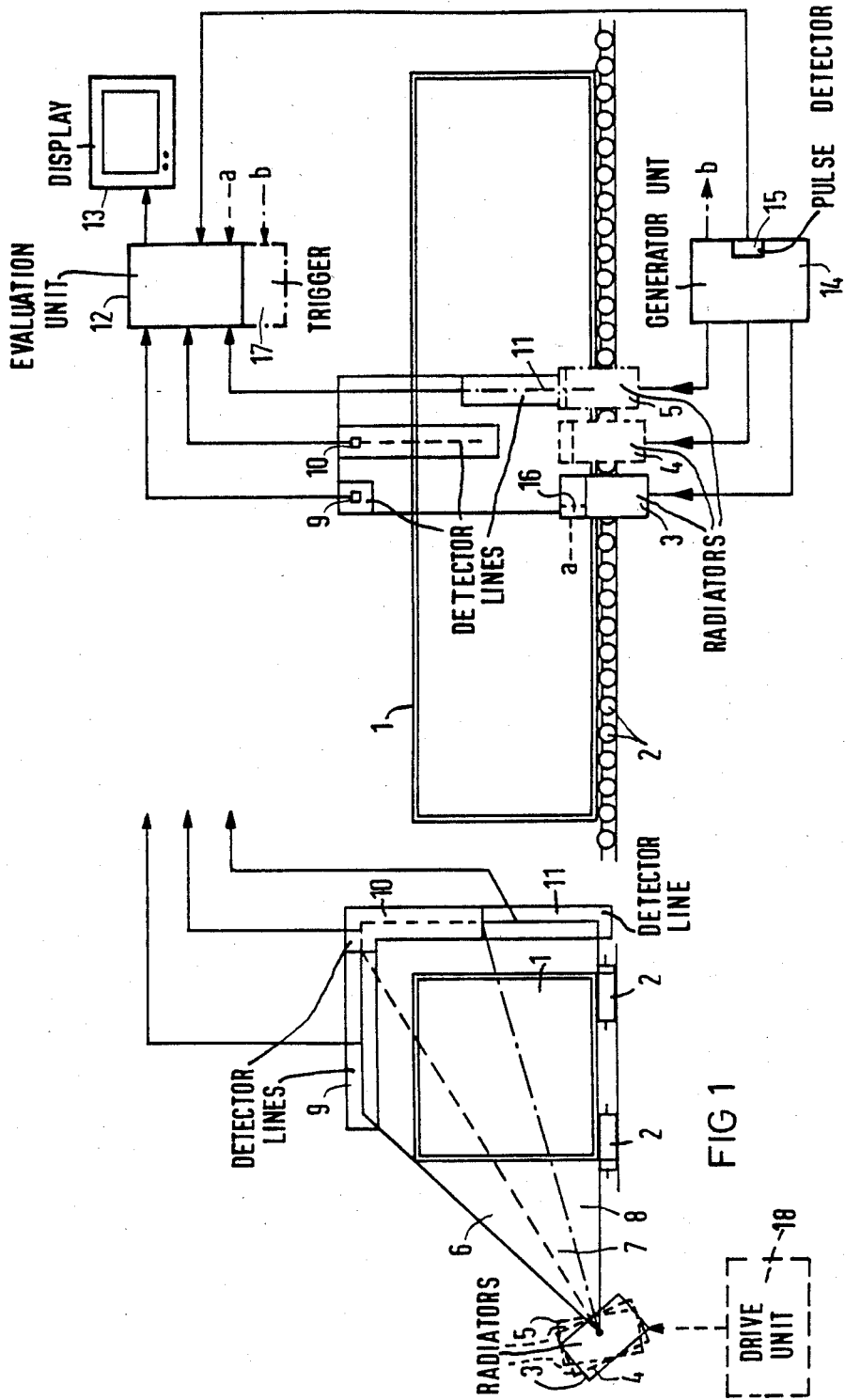

APPARATUS FOR TRANSRADIATING OBJECTS ON A CONVEYOR PATH

BACKGROUND OF THE INVENTION

1. Field of the Invention

The present invention relates to devices for transradiating objects moving on a conveyor path, such as containers, and in particular to an apparatus for transradiating such objects with a fan-shaped radiation beam disposed substantially perpendicularly to the direction of conveyance of the objects.

2. Description of the Prior Art

A device for transradiating containers moving on a conveyor device with a fan-shaped radiation beam disposed substantially perpendicularly to the direction of movement of the containers is described in U.S. Pat. No. 4,430,568. In this device, a linear accelerator must be employed as the radiator for transradiating large containers. Typical linear accelerators generally have an emission angle in the range of about 15° to about 20° due to inherent limitations. In order to transilluminate an entire container, an extremely large distance is required between the radiator and the receiver. Because of the large distance, the intensity at the radiation receiver is generally not sufficient to monitor filled containers. Another possibility is to undertake partial transilluminations of the object by a meandering relative motion between the container and the system including the radiator and the receiver. An overall image, however, cannot be generated by this techinque because the sub-images always partially overlay. Moreover, repeated back and forth movement of the container or of the radiator-receiver system is necessary. Lastly, tolerance problems exist as a result of the simultaneous movement of the radiator and the receiver, which movement must at least partially be undertaken in the vertical direction.

SUMMARY OF THE INVENTION

It is an object of the present invention to provide an apparatus transillumination of objects moving on a conveyor path which can transradiate even large freight containers.

It is a further object of the present invention to provide such an apparatus which can transradiate large freight containers with the lowest possible outlay in motion and time, and given the smallest possible dimensions for the protective radiation housing and the necessary high intensity at the radiation receiver.

It is a further object of the present invention to provide such an apparatus wherein an overall image of the entire container can be generated, so that the possibility of geometrical image magnification and/or of emphasizing specific gray scale values exists.

The above objects are inventively achieved in accordance with the principles of the present invention in an apparatus wherein the radiation receiver is formed of a plurality of detector lines which are disposed such that a portion of the radiation permeating a portion of the container is received by each detector line, and the entire radiation permeating the container is received by all of the detector lines in combination. Respective sub-regions of the object are transradiated by a plurality of radiation fan beams in one embodiment, and the corresponding radiation is received by one detector line for each fan. An overall image of the container is thereby acquired by combining the output signals of all of the detector lines.

For generating the radiation fans, a plurality of radiation radiators or generators can be disposed at a distance from each other in the direction of conveyance of the objects, offset relative to each other by the fan angle. In a further embodiment of the invention, however, only one radiator may be utilized, this single radiator being pivotably mounted for rotation around an axis parallel to the direction of conveyance. In order to prevent scatter radiation from influencing the quality of the image, the detector lines can be switched to a sensitive or receiving status by suitable delays so that the detectors are in a receiving status only when primary radiation is incident thereon.

DESCRIPTION OF THE DRAWINGS

FIG. 1 is an end view of an apparatus for transradiating objects moving on a conveyor path constructed in accordance with the principles of the present invention.

FIG. 2 is a side view of the apparatus shown in FIG. 1.

DESCRIPTION OF THE PREFERRED EMBODIMENTS

An apparatus for transradiating objects moving on a conveyor path constructed in accordance with the principles of the present invention is schematically represented in side view in FIG. 1. An object 1, such as a container, is transported in the longitudinal direction on a conveying path 2, such as formed by a roller conveyor. Three radiators, 3, 4 and 5, each of which generates a radiation fan of penetrating radiation are provided for transradiating the container 1. The radiators 3, 4 and 5 may be, for example, linear accelerators. The radiator 3 generates a radiation fan 6, the radiator 4 generates a radiation fan 7, and the radiator 5 generates a radiation fan 8. The radiation fans 6, 7 and 8 each have a central or main axis which is substantially perpendicular to the direction of conveyance of the objects 1, meaning when viewed from above, the central axes form right angles with that conveyance direction. As shown in FIG. 1, each of the radiation fans 6, 7 and 8 is disposed parallel to the plane containing the drawing, and the direction of object conveyance extends perpendicularly out of the plane of the drawing.

Three detector lines 9, 10 and 11 are disposed opposite the radiators 3, 4 and 5 with the object 1 moving therebetween. The detector lines 9, 10 and 11 receive radiation after passing through the object 1. The lines 9, 10 and 11 are arranged to form an angle in a known manner. Each detector line may be formed by an array, such as a row, of individual sensors for ionizing radiation. The detector line 9 receives radiation from the fan 6, the detector line 10 receives radiation from the fan 7, and the detector line 11 receives radiation from fan 8. The output signals of the detector lines 9, 10 and 11 are connected to an evaluation unit 12 for evaluating the signals and generating an overall image of the object 1 on a monitor 13. Feed and control of the radiators 3, 4 and 5 is undertaken by a generator unit 14.

Examination of an object 1 is undertaken such that the entire length of the object 1 is moved past the radiators 3, 4 and 5 and the detector lines 9, 10 and 11. The evaluation unit 12 constructs a shadowgraph of the object 1, and reproduces it on the monitor 13. Because each detector line 9, 10 and 11 respectively receives radiation which has permeated only one portion of the object 1, and the entire permeating radiation is received by all of the detectors 9, 10 and 11 in combinaton, it is possible to construct an overall survey image of the object 1 from the sub-images which are generated by the radiation fans 6, 7 and 8. The radiators 3, 4 and 5 accordingly, may be moved relatively close to the conveying path 2. The radiators 3, 4 and 5 are disposed at a distance from each other in the direction of conveyance of the objects 1, and are rotated relative to each other along an axis parallel to the conveyance direction by the fan angle of the radiation fans 6, 7 and 8. It is also possible to utilize only a single radiator, for example the radiator 3, and in that embodiment the radiator 3 includes a drive unit 18 for rotating the radiator 3 about the axis parallel to the conveying direction. The radiation fan emitted by the rotated radiator 3 successively transradiate the various parts of the object 1 when the object 1 is at rest. In this embodiment, the detector lines 9, 10 and 11 are not disposed next to each other as shown in FIG. 2, but rather all lie in a single plane. Also in this embodiment, the object 1 must be repeatedly shifted back and forth along the conveyor path in order to generate a complete image.

In the illustrated exemplary embodiment, the detector lines 9, 10 and 11 can be automatically switched to a sensing or receiving state by the evaluation unit 12 at a time when each line is to be impinged by primary radiation. For this purpose, the evaluator unit 12 may be provided with a pulse detector 15 in the generator 14 allocated thereto for detecting radiation pulses and thereby acquiring a count corresponding to the respective on times of the radiators 3, 4 and 5. An alternative is the use of radiation detectors which acquire respectively occurring radiation disposed at the radiation exit windows of the radiators 3, 4 and 5. Such a radiation detector is shown in FIG. 2 for the radiator 3 referenced at 16. The radiation detector 16 is connected via a line a to the evaluator unit 12. A trigger 17 may also be utilized for effecting synchronous turn-on of one of the radiators 3, 4 and 5 and of the allocated detector line 9, 10 and 11. The trigger 17 is connected to the generator 14 via line b. The radiators 3, 4 and 5 are successively pulsed.

In order to store an overall image in a memory of the evaluator unit 12, the sub-images generated by the detector lines 9, 10 and 11 may be entered with a chronological offset corresponding to the originating location.

Linear accelerators generally emit pulsed radiation with a duty cycle of approximately 1:1000. In order to above influencing the image quality due to scatter radiation, the reception channels of a detector line 9, 10 and 11 may be switched to a sensing state as described above only for the duration of the pulse time of the associated radiator 3, 4 or 5. Again, the radiators 3, 4 and 5 are operated by the generator 14 to successively emit their radiation pulses.

Although modifications and changes may be suggested by those skilled in the art it is the intention of the inventors to embody within the patent warranted hereon all changes and modificatons as reasonably and properly come within the scope of their contribution to the art.

We claim as our invention:

1. An apparatus for tranradiating an object moving on a conveyor path comprising:
    means for generating a plurality of fan-shaped radiation beams directed at said object and disposed substantially perpendicularly to said conveyor path each beam irradiating a respective substantially non-overlapping portion of said object and said beams in combination completely irradiating said object;
    a plurality of line-shaped radiation detectors disposed for receiving radiation after passing through the respective portions of said object with radiation passing through one of said respective portions of said object being received by only one of said detectors, and all of said detectors in combination receiving the radiation passing through all of said respective portions of said object; and
    means connected to said detectors for evaluating signals therefrom to construct a complete image of said object.

2. An apparatus as claimed in claim 1, wherein said means for generating comprises a plurality of radiators disposed at distances from each other in a direction of conveyance on said conveyor path, each radiator being rotated about an axis parallel to said conveyor path by an angle such that all said fan-shaped radiation beams in combination completely irradiate said object, and wherein said detectors are also disposed at distances from each other corresponding to the distances of said radiators.

3. An apparatus as claimed in claim 1, wherein said means for generating includes only one radiator and a means for pivoting said radiator about an axis parallel to the direction of conveyance to generate said fan-shaped beams in one plane, and wherein said radiation detectors are disposed in a plane containing the fan-shaped radiation beams generated by said radiator.

4. An apparatus as claimed in claim 1, further comprising a control means for said radiation detectors for switching said detectors to a sensing status at a selected time when primary radiation is incident thereon.

5. An apparatus as claimed in claim 4, wherein said control means includes a radiation pulse detector for detecting the appearance of radiation pulses from said means for generating, said pulse detector being connected to said means for evaluating for switching said detectors to and from receiving status.

6. An apparatus as claimed in claim 5, further comprising a generator unit for controlling operation of said means for generating, and wherein said control means is disposed in said generator unit for selectively operating said means for generating in a specified sequence.

7. An apparatus as claimed in claim 5, wherein said pulse detector is disposed at a radiation exit window of said means for generating.

8. An apparatus as claimed in claim 4, further comprising a trigger means for synchronizing turn-on of said means for generating with a selected detector.

9. An apparatus for transradiating an object moving on a conveyor path comprising:
    a plurality of radiation generators for generating radiation for permeating said object, each radiation generator being offset with respect to the other generators along an axis parallel to the direction of conveyance of objects on said conveyor path, and each generator being oriented by rotation about said axis for directing a fan-shaped radiation beam at a portion of said object substantially perpendicularly to said conveyor path, each beam irradiating a respective portion of said object and the beams in combination completely irradiating said object;
    a like plurality of line-shaped radiation detectors disposed offset with respect to each other by distances equal to the offset of said radiation generators for respectively receiving radiation from said radiators after passing through said respective portions of said objects, radiation passing through one of the respective portions of said object being received by only one of said detectors, and all of said detectors in combination receiving the radiation passing through all of said respective portions of said object; and an evaluator means connected to said detectors for evaluating and combining signals therefrom to construct a complete overall image of said object.

10. An apparatus for transradiating an object as claimed in claim 9, further comprising a generating unit connected to said radiation generators for successively pulsing said radiation generators.

11. An apparatus for transradiating an object as claimed in claim 10, further comprising means connected to said detectors for synchronizing operation of said detectors to a receiving status only when the radiation generator associated therewith is pulsed.

* * * * *